(12) United States Patent
Triva

(10) Patent No.: US 10,220,390 B2
(45) Date of Patent: Mar. 5, 2019

(54) DEVICE FOR COLLECTING AND TRANSFERRING SAMPLES OF BIOLOGICAL MATERIAL

(71) Applicant: Copan Italia S.p.A., Brescia (IT)

(72) Inventor: Daniele Triva, Bovezzo (IT)

(73) Assignee: Copan Italia S.p.A., Brescia (IT)

( * ) Notice: Subject to any disclaimer, the term of this patent is extended or adjusted under 35 U.S.C. 154(b) by 733 days.

(21) Appl. No.: 13/926,230

(22) Filed: Jun. 25, 2013

(65) Prior Publication Data

US 2013/0344616 A1    Dec. 26, 2013

(30) Foreign Application Priority Data

Jun. 26, 2012    (IT) .............................. MI2012A1120

(51) Int. Cl.
*A61B 10/00* (2006.01)
*B01L 3/00* (2006.01)

(52) U.S. Cl.
CPC ........ *B01L 3/5055* (2013.01); *A61B 10/0045* (2013.01); *B01L 3/5023* (2013.01); *A61B 10/0051* (2013.01); *A61B 10/0096* (2013.01); *Y10T 436/25* (2015.01)

(58) Field of Classification Search
None
See application file for complete search history.

(56) References Cited

U.S. PATENT DOCUMENTS

| 4,963,325 | A |  | 10/1990 | Lennon et al. |
| 5,169,789 | A | * | 12/1992 | Bernstein ........... G01N 33/5302 422/413 |
| 5,308,580 | A |  | 5/1994 | Clark |
| 5,766,962 | A | * | 6/1998 | Childs ............... A61B 10/0038 436/518 |
| 8,998,824 | B2 | * | 4/2015 | Pierce ............... A61B 10/0045 600/572 |

(Continued)

FOREIGN PATENT DOCUMENTS

| EP | 1608268 | 11/2007 |
| EP | 1870160 | 12/2007 |
| WO | WO9003959 | 4/1990 |
| WO | WO 2008/099196 | 8/2008 |
| WO | WO-2012163788 A1 * 12/2012 ......... A61B 10/0045 |

OTHER PUBLICATIONS

Authorized officer Nina Jansson Godoy, Search Report and Opinion in Italian Application No. MI20121120, dated Jun. 26, 2012, 10 pages, report dated Feb. 14, 2013.

*Primary Examiner* — Christopher Adam Hixson
*Assistant Examiner* — Michelle Adams
(74) *Attorney, Agent, or Firm* — Fish & Richardson P.C.

(57) ABSTRACT

A device for collecting, transferring and/or conserving samples of biological material, comprising at least: a support body having at least a housing seating for a conserving element for samples, the housing seating being configured for enabling removably housing the conserving element for samples of biological material, the support body being configured for maintaining at least a conserving portion of the conserving element accessible for depositing a sample when the conserving element is housed in the housing seating; an operating portion, movable between a first closed position in which it is arranged in proximity of said housing seating and at least an open position in which it is arranged in a distanced position from the housing seating; and engaging portion configured for selectively and removably engaging a sampling element for samples, in particular an element for buccal sampling, to the support body and/or to the operating portion.

14 Claims, 5 Drawing Sheets

(56) References Cited

U.S. PATENT DOCUMENTS

2004/0161855 A1\* 8/2004 Kvasnik .................. B01L 3/545
                                                                 436/165
2004/0171173 A1\* 9/2004 Eckermann ........ A61B 10/0045
                                                                 436/514

\* cited by examiner

FIG.4
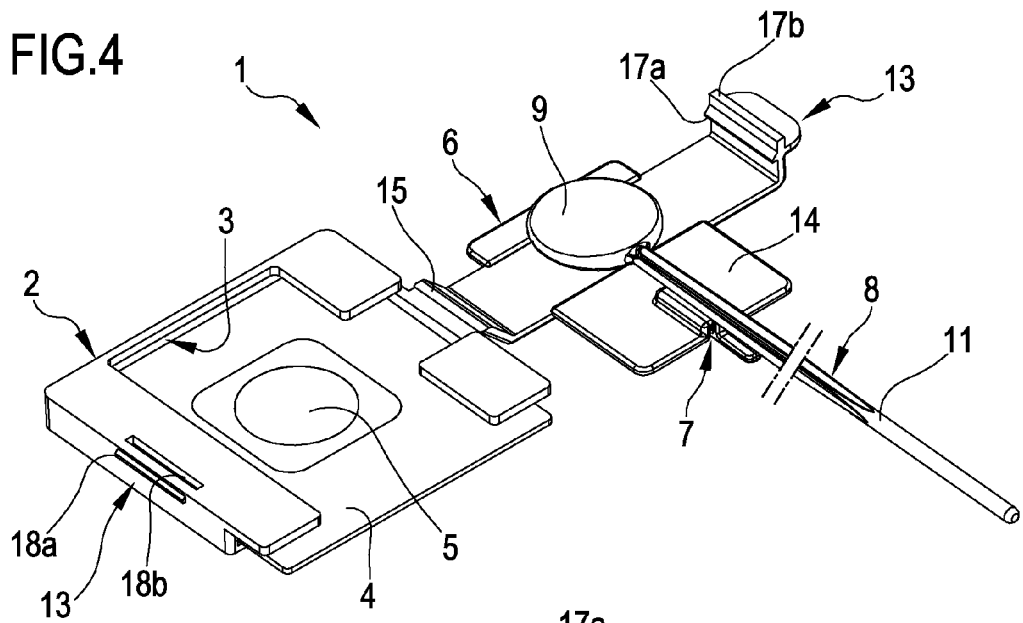
FIG.5
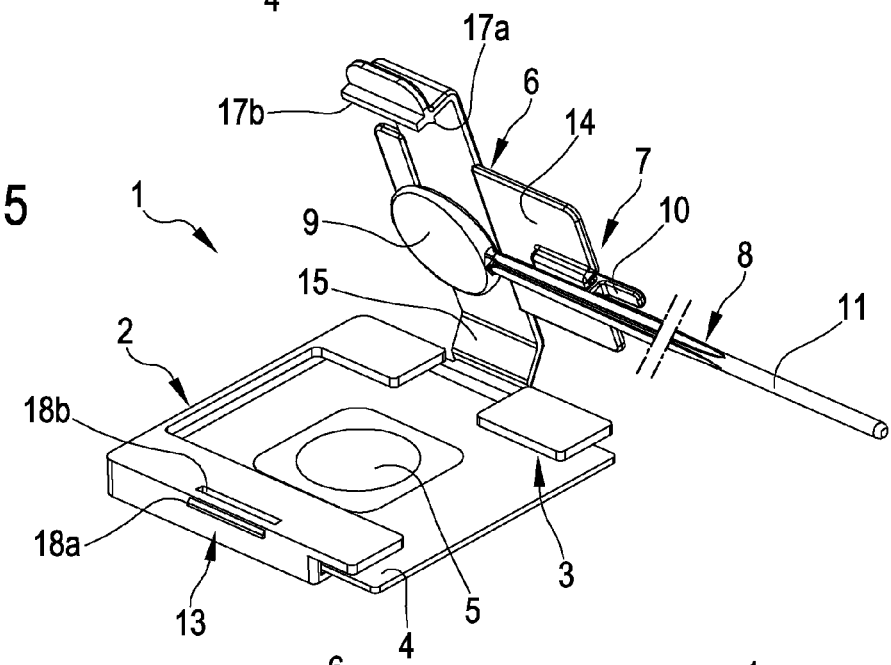
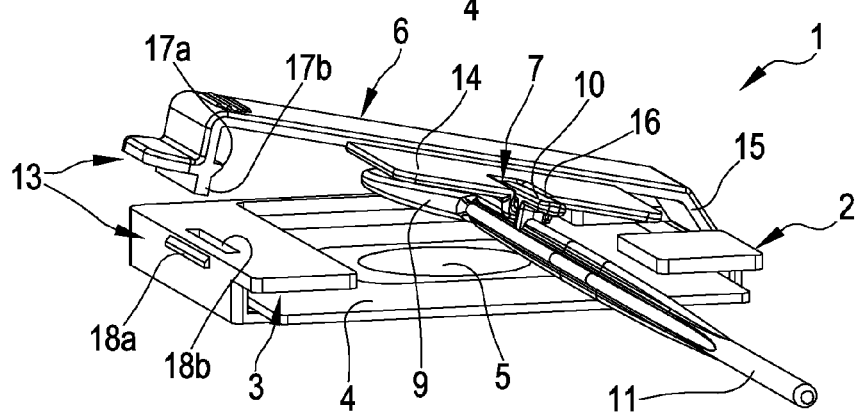
FIG.6

FIG.10
FIG.11
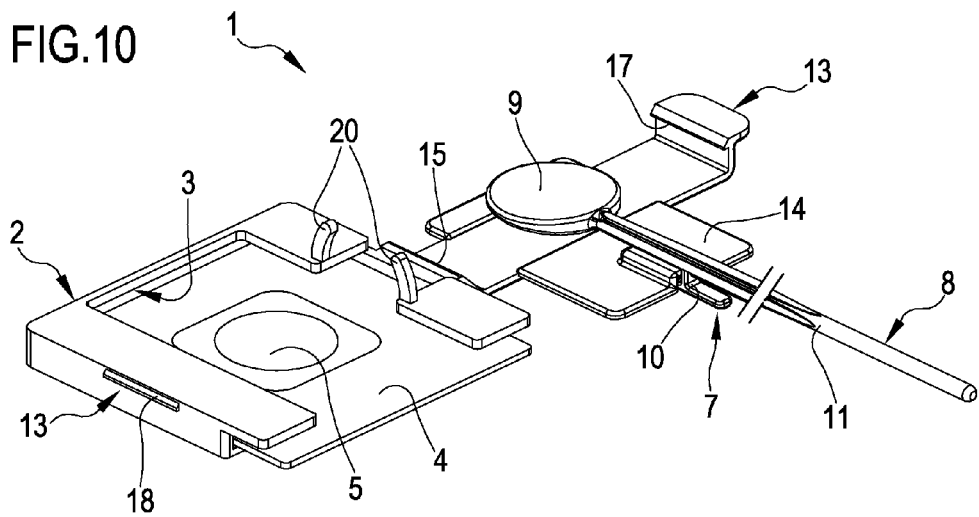
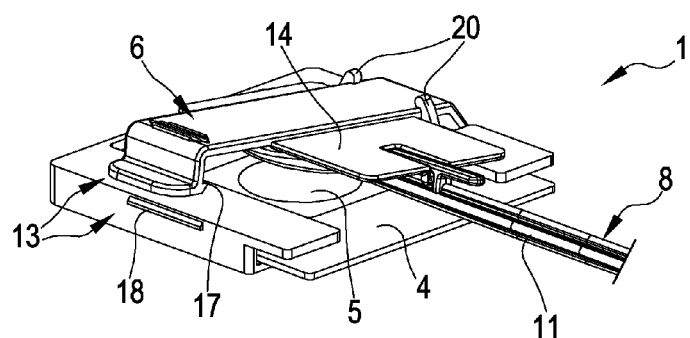
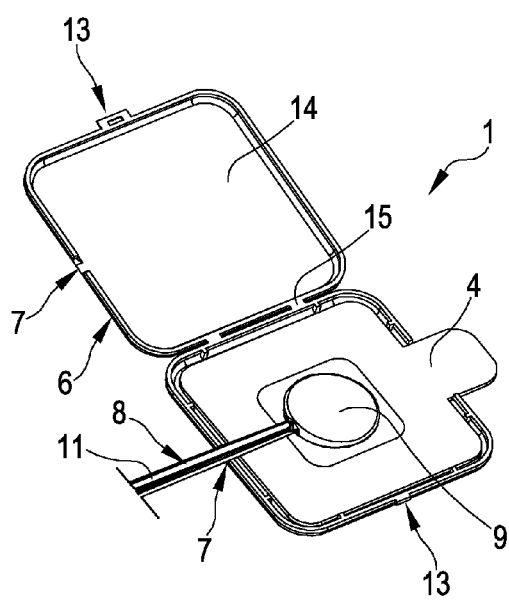
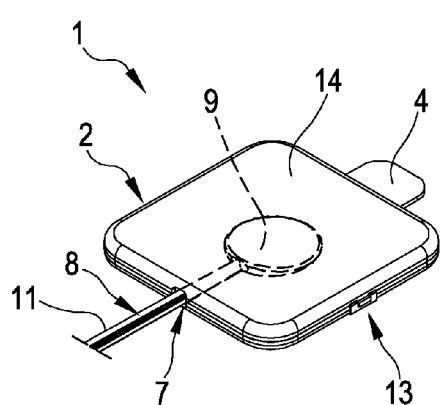
FIG.12         FIG.13

DEVICE FOR COLLECTING AND TRANSFERRING SAMPLES OF BIOLOGICAL MATERIAL

CROSS-REFERENCE TO RELATED APPLICATION

The present application claims priority under 35 U.S.C. § 119 of Italian Application No. MI2012A001120, filed Jun. 26, 2012. Applicant incorporates the entire disclosure the prior application by reference herein.

DETAILED DESCRIPTION

The present invention relates to a device for collecting, transferring and/or conserving samples of biological material.

The invention further relates to a method for collecting, transferring and/or conserving samples of biological material by means of the device and a use of the device for collecting, transferring and/or conserving samples of biological material. The invention is in particular applicable to collection, transfer and/or conservation of buccal or lingual samples.

Use is known of conventional sampling devices which are provided at least with a collecting portion able to collect biological samples and a support body enabling manipulation of the collecting element.

Collecting devices are known which have collecting portions of various different types, for example constituted by cotton fibres wound about a stick, or an absorbent material of a spongey or foamy type mounted on the stick, etc.

Also known are devices known as "flocked swabs", comprising an elongate support body and a plurality of flocked fibres at an end of the support body such as to define a collecting portion for the analytes or biological samples. This type of device is known from patent EP1608268 (TRIVA).

It is further known, after having collected the sample of biological material, to transfer the biological sample onto a different support that can enable conserving the biological sample even for a long period of time. For example it is known for the collected samples by means of the collecting devices on matrix supports or chemically-treated papers to enable absorption and conservation of the samples of biological material. This type of paper is known, for example, from patent application WO9003959 (BURGOYNE).

Also known are devices enabling collecting the biological sample and the transfer thereof onto the papers for conservation by means of a single device, which comprises both the sample element and a support for the paper. This device, known for example from patent application WO2008/099196 (HARVERY et al), comprises a connecting portion between the collecting element and the paper support, which connecting portion can be bent after performing the sample in order to bring the collecting portion of the collecting element into contact with the paper, and effecting the transfer of the sample of biological material collected on the paper.

This solution enables guaranteeing traceability of the collected sample, as the collecting element and the relative paper, housed in the support solidly constrained to the device, can be kept together, with no possibility of error in the transfer.

The above-described device exhibits some drawbacks however. In fact, as this is a single device, it is unwieldy in use for collecting the sample, as the operator constantly has to manipulate all the device during the collection of the sample, including the support, and not only the collecting element. This is particularly difficult in the typical case of use of the device, i.e. where a buccal sample is to be collected inside a patient's mouth. Further, this leads to the risk of contaminating the paper housed in the support during the manipulation of the device for collecting the sample.

The main aim of the present invention is to obviate one or more of the problems encountered in the prior art.

An aim of the present invention is to provide a device and a method for collecting, transferring and/or conserving samples of biological material, which are easy to use and realize.

A further aim of the present invention is to provide a device and method for collecting, transferring and/or conserving samples of biological material which enable a reduction in the risk of contamination of the collected samples.

A further aim of the present invention is to provide a device and a method for collecting, transferring and/or conserving samples of biological material which enable traceability of collected samples.

A further aim of the present invention is to make available a device and a method for collecting, transferring and/or conserving samples of biological material which are simple and economical to realise.

These aims and others besides, which will more fully emerge from the following description, are substantially attained by a device and a method for collecting, transferring and/or conserving samples of biological material according to what is set down in one or more of the accompanying claims, taken alone or in combination with one another, or in any combination with one or more of the further aspects described in the following.

In a further aspect, the invention further relates to a device for collecting, transferring and/or conserving samples of biological material according to any one of the appended claims, and/or the further aspects indicated herein, further comprising at least an identifying label or other identifying element.

In a further aspect, the invention further relates to a device according to any one of the accompanying claims, and/or the further aspects indicated herein, in which a housing seating for a conserving element for sample of biological material is configured as a lateral opening of a support body in which the conserving element in the form of paper, e.g., a card, is insertable by element.

In a further aspect thereof, the invention further relates to a method according to any one of the accompanying claims, and/or the further aspects indicated here, further comprising a step of distancing the collecting portion of the collecting element from the conserving portion of the conserving element in order to bring the device for collecting and transferring samples of biological material into a conserving and/or transport position.

In a further aspect, the invention further relates to a method according to any one of the accompanying claims, and/or the further aspects indicated herein, further comprising the step of conserving the sample of biological material on the conserving portion of the conserving element for a prolonged time interval and/or with the collecting device and/or conserving samples of biological material configured in a position of conservation or transport.

In a further aspect thereof, the invention further relates to use of a device according to any one of the accompanying claims for collection, transfer and/or conservation of a sample of biological material and/or for buccal collection, transport and conservation of a sample of buccal biological material.

BRIEF DESCRIPTION OF THE DRAWINGS

By way of non-limiting example, a description is now provided of one or more preferred embodiments of the invention, in which:

FIG. 4 illustrates a device of FIG. 3 with the collecting element coupled with an engaging portion of the operating portion;

FIGS. 5 and 6 show the device of FIG. 4 in two respective intermediate positions between the open position and a closed position;

FIG. 10 shows a variant of the device of FIG. 3 in an open position, with a collecting element coupled with an engaging portion of the operating portion;

FIG. 11 illustrates the device of FIG. 10 in an intermediate position between the open position and a closed position;

FIG. 12 shows a further variant of the device of FIG. 3 in an open position, with a collecting element coupled with an engaging portion of the support body;

FIG. 13 shows the device of FIG. 12 in a closed position.

Figure 1:
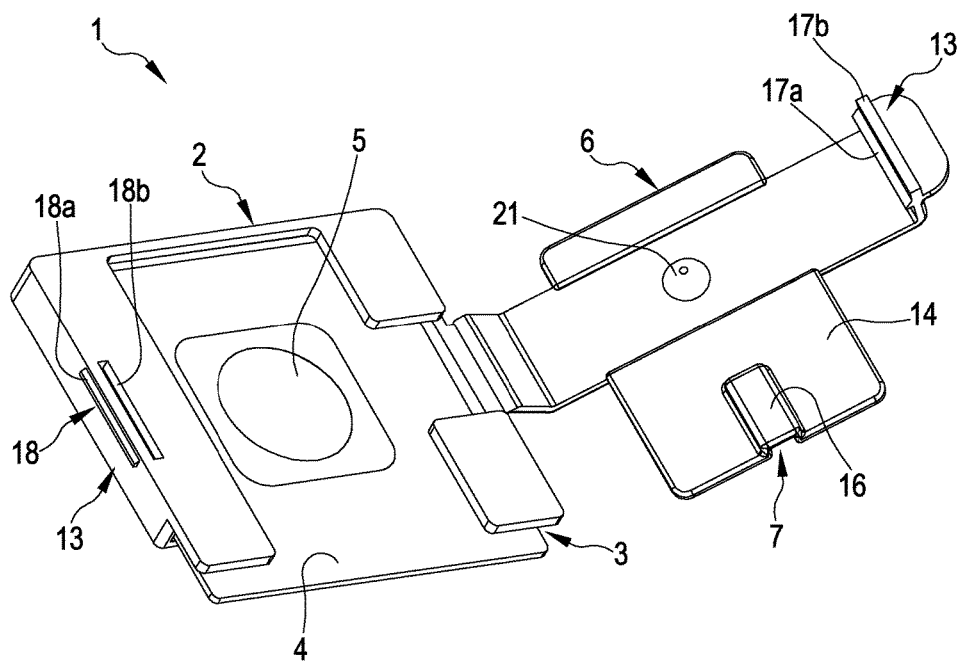
FIG. 1 is a front perspective view of a support body and a mobile operating portion of a device according to an embodiment of the present invention, in an open configuration.

With reference to the accompanying figures of the drawings, 1 denotes in its entirety a device for collecting, transferring and/or conserving samples of biological material.

The device comprises at least a support body 2 having at least a housing seating 3 for a conserving element 4 of biological samples. The seating 3 is configured to enable the housing to removably accommodate the conserving element 4 of biological samples.

The conserving element 4 is preferably a chemically-treated paper, e.g., a card, and is suitable for the conservation of samples of biological material, and in particular is a paper comprising at least a conserving substance for a sample of biological material, in particular suitable for conserving of a buccal sample. The housing seating 3 can thus be configured to removably accommodate the chemically-treated paper for the conservation of biological samples, and preferably is configured as a lateral opening of the support body 2 in which the paper is inserted by sliding.

The support body 2 is configured to maintain at least a conserving portion 5 of the conserving element 4 accessible for depositing a sample of biological material when the conserving element 4 is housed in the housing seating 3, for example through a front opening 12, with respect to the lateral opening.

The device 1 further comprises an operating portion 6 movable at least between a first closed position in which it is arranged in the vicinity of the housing seating 3 and at least an open position in which is arranged in a distanced position from the housing seating 3.

The device 1 further comprises an engaging portion 7 configured to selectively and removably engage a sampling element 8 for samples of biological material to the device 1 for the collection and transfer of samples of biological material, and in particular to the support body 2 and/or to the operating portion 6.

The sampling element 8 is provided with at least a collecting portion 9 suitable for collecting samples of biological material, with an elongate body 11 to enable manipulation, and at least a coupling portion 10 at which it is selectively and removably coupled 7 to the engaging portion 7.

In particular, the element 8 can be a collecting device for a buccal sample, or a buccal swab. In the present text "buccal" is taken to mean a collection of a biological sample that is performed in a patient's mouth, and therefore also includes a lingual sample or the like.

The invention can however find application, in one or more of its aspects, for samples of a type other than buccal, for example from other body cavities, or for collection of blood samples. In a further embodiment, shown in FIGS. 12 and 13, the engaging portion 7 can be configured to selectively and removably engage the sampling element 8 to the support body 2 and/or be realised directly on the support body 2, in proximity of the housing seating 3, so that the collecting portion 9 is located at the conserving portion 5.

Further, the engaging portion 7 can be used to define at least a first mounting position of the sampling element 8 at which contact occurs and a transfer of biological material is made between the collecting portion 9 and the conserving portion 5. The engaging portion 7 is also able to define at least a second mounting position of the collecting element at which the collecting portion 9 is distanced from the conserving portion 5 and therefore there is no contact and transfer of biological material between the collecting portion 9 of the sampling element 8 and the conserving portion 5, the second mounting position further defining a conserving and/or transport position of storage of the device 1.

In the embodiments shown in FIGS. 1 to 11, the engaging portion 7 is configured to selectively and removably engage the collecting element 8 for samples of biological material to the operating portion 6, so that the sampling element 8 is selectively portable, in consequence of the displacing of the operating portion 6, at the housing seating 2 and the conserving portion 5 in the first closed position and/or in such a way that the collecting portion 9 is selectively portable at the housing seating 3 and/or in contact with the conserving portion 5 in the first closed position.

Figure 8:
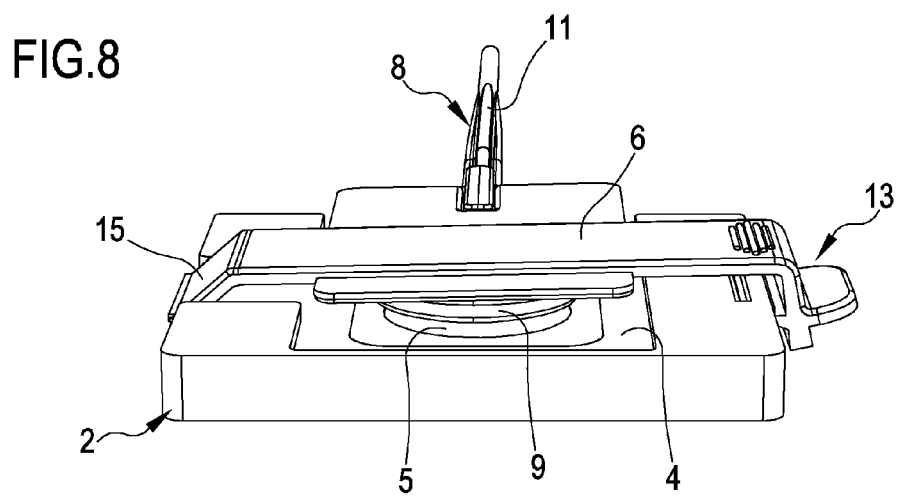
FIG. 8 is a detail of the device of FIG. 4 in a first closed position and/or contact and transfer position of the sample.
Figure 9:
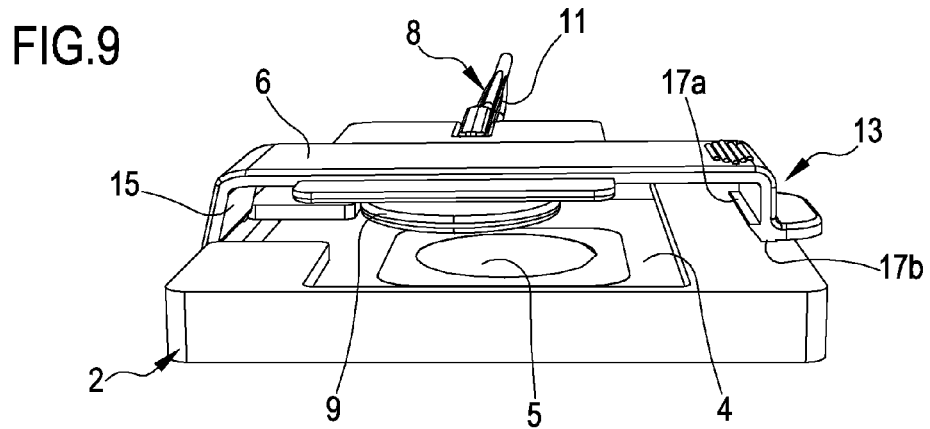
FIG. 9 is a detail of the device of FIG. 4 in a second closed position and/or conservation and transport position of the device.

The device can further comprise a closing portion 13 for selectively closing the device 1 at least in the first closed position, illustrated in detail in FIG. 8, in which there preferably occurs a contact and a transfer of biological material between the collecting portion 9 and the conserving portion 5. The closing portion 13 is preferably also able to further define at least a second closed position, illustrated in detail in FIG. 9, in which the collecting portion 9 is distanced from the conserving portion 5 and therefore there is no contact and transfer of biological material between the two portions, the second closed position advantageously also defining a conserving and/or transport position of the device 1.

The operating portion 6 can comprise an closing element 14, or lid, able at least in the first closed position and/or in the second closed position to at least partially cover the housing seating 3 and/or at least partially cover and protect the conserving element 4 for samples of biological material housed in the housing seating 3 and/or to cover and protect the conserving portion 5 for samples of biological material during storage and/or transportation of the device and/or at least in the second closing position and/or at least in the second mounting position.

The operating portion 6 can be non-removably engaged to the support body 2, for example, can be realized in a single piece with the support body 2. In a variant the operating portion 6 can be removably engaged to the support body 2. In the embodiments illustrated in the accompanying figures, the operating portion 6 is joined to the support body 2 by means of an elastically deformable connecting portion 15. In a variant, the connecting portion 15 can be plastically deformable. At least the support body 2, the operating portion 6, the engaging portion 7, the connecting portion 15, the sampling element 8 and/or the coupling portion 10 are preferably made of plastic material. For example, the support body 2, the operating portion 6, the engaging portion 7 and the connecting portion 15 can be made of polypropylene, while the sampling element 8 and/or the coupling portion 10 can be made of polystyrene.

The engaging portion 7 can for example include a seating 16 in which the coupling portion 10 of the sampling element 8 is selectively insertable by sliding and/or snap-fitting and/or rotation, or in any other way suitable for the purpose. Also, and alternatively, a coupling seating could be provided on the sampling device and a coupling portion 7 on the engaging portion. The closing portion 13 can comprise at least a coupling portion 17 made on the operating portion 6 and at least a hooking seating 18 realised on the support body 2. Also, and alternatively, a coupling seating could be provided on the operating portion 6 and an engagement portion on the support body 2.

The closing portion 13 can comprise at least two distinct engaging portions 17a, 17b selectively engageable in the hooking seating 18, such as to define respectively the first and the second closed position. The closing portion 13 can comprise at least two separate hooking seatings 18a, 18b with the engagement portion 17 to define respectively the first and the second closed position. In the embodiment of FIGS. 1-9, the hooking portion 17 comprises at least two distinct hooking zones 17a, 17b, designed each to engage with a respective distinct hooking seating 18a, 18b to define respectively the first and the second closed position (illustrated respectively in FIGS. 8 and 9). In the variant of FIGS. 10 and 11, the first closed position is defined by a hooking portion 17 and a corresponding hooking seating 18, while the second closed position is instead defined by additional sealing elements 20 acting on the operating portion 16 and/or on the connecting portion 15, defining the above-mentioned second closed position (at which the hooking portion 17 is not engaged with the hooking seating 18).

Figure 2:
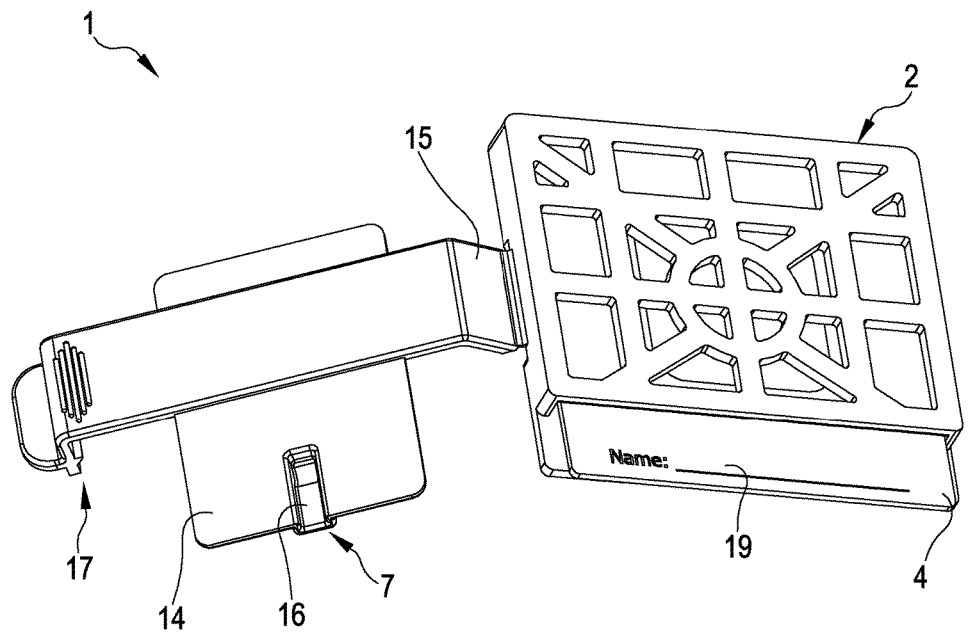
FIG. 2 is a rear perspective view of the support body and the mobile operating portion of FIG. 1.
Figure 3:
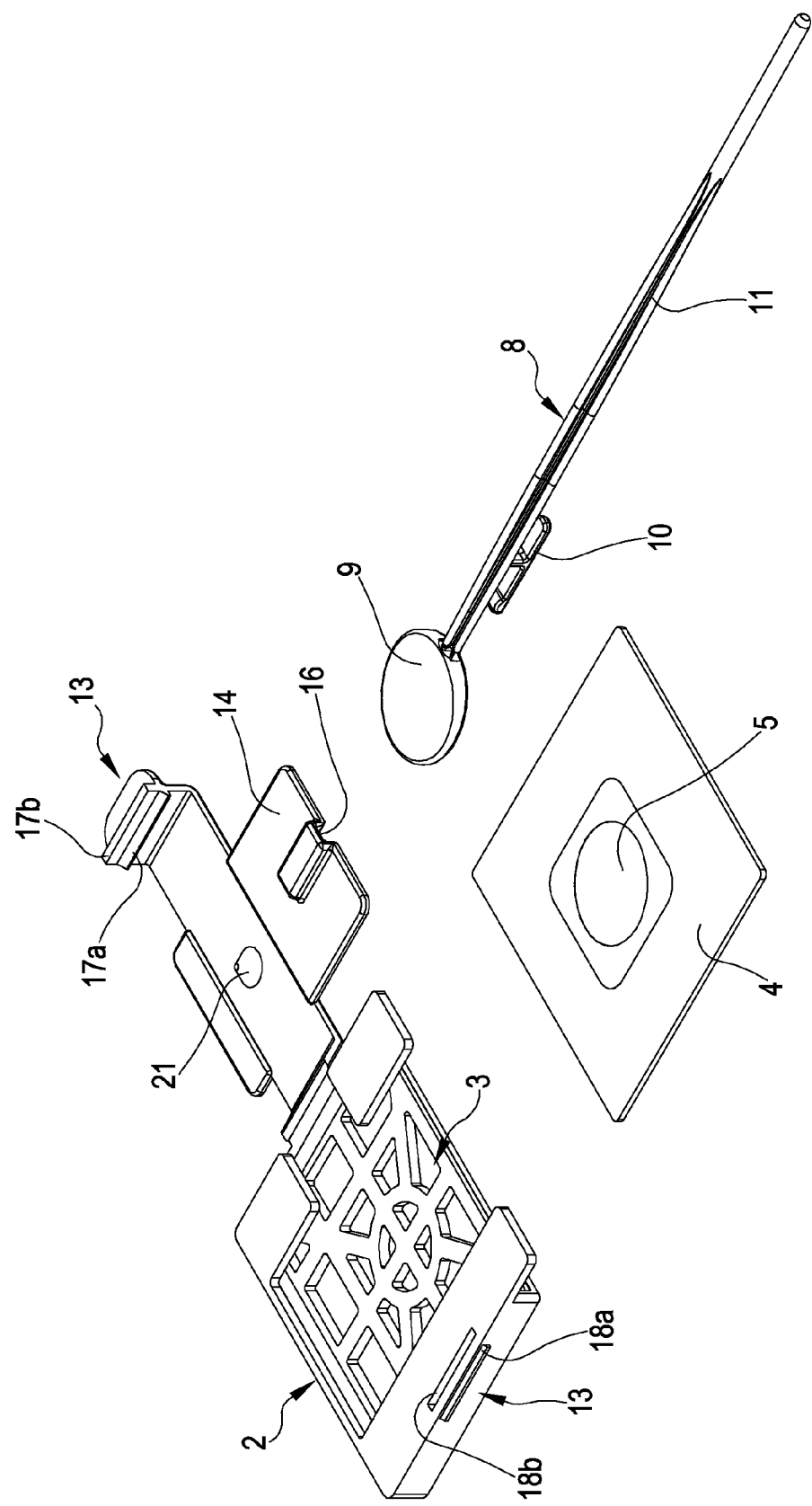
FIG. 3 is a device according to an embodiment of the present invention in an open position, with a collecting element not coupled with an engaging portion of the operating portion.
Figure 7:
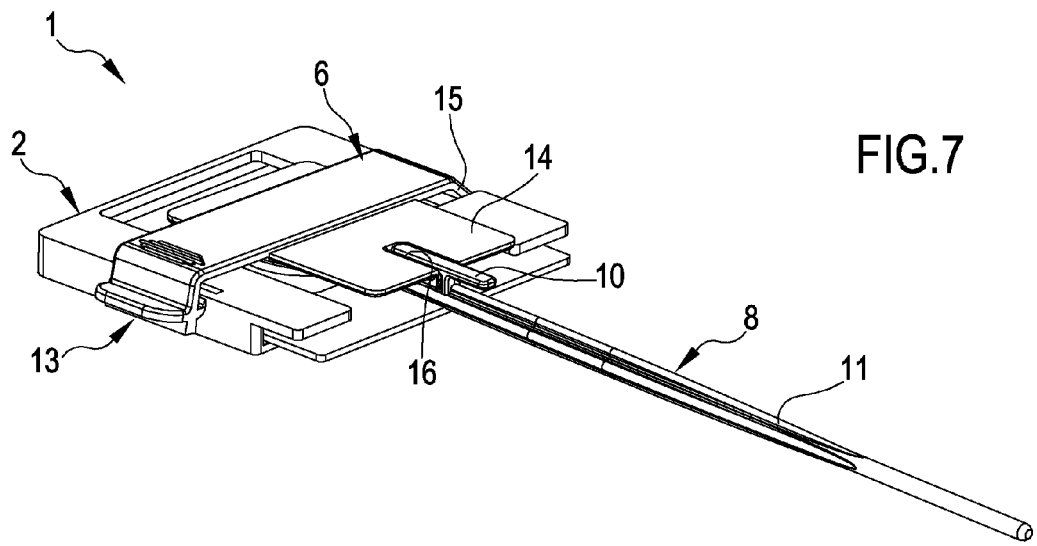
FIG. 7 is the device of FIG. 4 in a closed position.

The device 1 can further comprise a projecting element 21 of the operating portion 6 able to act on the collecting portion 9 so as to force it into contact with the conserving portion 5 and facilitate transfer of the biological material. The device 1 further can comprise at least an identifying label or other identifying element 19, which can be provided for example on the support body 2, and/or on the mobile operating portion 6, and/or on the conserving element 4, as shown in FIG. 2.

The invention also relates to a method for collection, transfer and/or the conserving of samples of biological material by means of a device 1 of the above-described type.

The method comprises at least following steps: collecting a sample of biological material on at least a collecting portion 9 of a sampling element 8, preferably a buccal sample, subsequently selectively coupling the sampling element 8 with a support body 2 or with a mobile operating portion 6 of the device 1, then bringing a portion 9 of the sampling element 8 collection into contact with a conserving portion 5 of a conserving element 4 of biological samples housed in a housing seating 3 support body 2 so as to transfer a quantity of the biological material from the collecting portion 9 of the sampling element 8 to the conserving portion 5.

The method can further comprise the step of subsequently distancing the collecting portion 9 from the storage portion 5 of the conserving element 4 so as to bring the device 1 into a conserving and/or transporting position. The method can further comprise the step of maintaining the sample of biological material on the conserving portion 5 for a time interval, preferably with the device 1 configured in a conserving or transport position.

The invention also relates to the use of a device 1 of the type described above, for collection, transfer and/or conserving of a sample of biological material and/or for buccal collection, transportation and conserving of a sample of biological buccal material.

The present invention enables obtaining at least one or more of the following advantages. First, the invention obviates one or more of the problems found in the prior art. The invention is also convenient to use and easy to implement, further simplifying the transfer and/or the conserving of samples of biological material, in particular in the case of buccal and therefore also lingual samples. The invention also reduces the risk of contamination of the samples collected, as the collecting element is handled independently and separately from the support body of the conserving element during collection of the sample. The invention also affords full traceability of the samples collected, as the collecting element can be coupled to the respective conserving element. Lastly, the invention is simple and economical to actuate.

The invention claimed is:

1. A device for collecting, transferring and/or conserving samples of biological material, wherein the device comprises at least:
    a conserving element for samples of biological material, which is a card configured for conserving samples of biological material;
    a support body having at least a card housing seating for said conserving element for samples of biological material, said housing seating being configured for enabling removably housing said conserving element for samples of biological material, said support body being configured for maintaining at least a conserving portion of said conserving element accessible for depositing a sample of biological material when the conserving element is housed in said housing seating;
    a sampling element for samples of biological material which is provided with at least a collecting portion suitable for collecting samples of biological material; and
    an operating portion, movable between at least a first closed position in which it is arranged in proximity to said housing seating and at least an open position in which it is arranged in a distanced position from said housing seating, the operating portion comprising an engaging portion configured for selectively and removably engaging said sampling element;

said sampling element being selectively and removably coupleable to said engaging portion;

wherein the device further comprises a closing portion suitable for selectively closing said device at least in said first closed position;

wherein, in said first closed position, a contact and a transfer of biological material occurs between said collecting portion and said conserving portion; and wherein said closing portion is suitable for further defining at least a second closed position wherein said collecting portion is distanced from said conserving portion and thus there is no contact and transfer of biological material between said collection portion and said conserving portion, said second closed position further defining a conserving and/or transporting position of said device; and wherein said sampling element comprises a coupling portion and said engaging portion comprises a coupling seating in which said coupling portion of said sampling element is selectively insertable by snap-fitting of the coupling portion with the coupling seating, or wherein said engaging portion comprises a coupling portion and said sampling element comprises a coupling seating in which said coupling portion of said engaging portion is selectively insertable by snap-fitting of the coupling portion with the coupling seating.

2. The device of claim 1, wherein said engaging portion is configured for selectively and removably engaging said sampling element for samples of biological material to said operating portion, such that said sampling element can be selectively brought in proximity to said housing seating and to said conserving portion in said first closed position.

3. The device of claim 1, wherein said operating portion comprises a closing element or lid suitable for at least partly covering said housing seating, at least in said first closed position and/or in said second closed position.

4. The device of claim 3 wherein said closing element or lid at least partly covers and protects said conserving element for samples of biological material and/or wherein said closing element or lid covers and protects said conserving portion for samples of biological material during the conservation and/or transport of the device and/or wherein said closing element or lid covers and protects said conserving portion for samples of biological material at least in said second closed position and/or at least in a second assembling position.

5. The device of claim 1, wherein said operating portion is unremovably engaged to said support body and/or wherein said operating portion is realised in a single piece with said support body.

6. The device of claim 1 wherein said operating portion is removably engaged to said support body.

7. The device of claim 1 wherein said operating portion is joined to said support body by a connecting portion that is elastically deformable or plastically deformable.

8. The device of claim 1, wherein said coupling portion is selectively insertable in said coupling seating by sliding and/or by rotation, or vice versa.

9. The device of claim 1 wherein one or more of the following is made of a plastic material: (i) said device; (ii) said support body; (iii) said operating portion; (iv) said engaging portion; (v) a connecting portion joining said operating portion to said support body; (vi) said sampling element; or (vii) said coupling portion.

10. The device of claim 1 wherein said closing portion comprises at least a hooking portion realised on said operating portion and at least a hooking seating realised on said support body, or vice versa.

11. The device of claim 10 wherein said closing portion comprises two distinct hooking portions selectively engageable with said hooking seating so as to respectively define first and second closed positions, or wherein said closing portion comprises at least two hooking seatings realised on said support body for cooperating with said hooking portion in order to respectively define first and second closed positions, or wherein said closing portion comprises at least two hooking seatings realised on said support body for each cooperating respectively with one of two distinct hooking portions in order to respectively define first and second closed positions.

12. The device of claim 1, wherein said sampling element for samples of biological material is an element for buccal sampling or a buccal swab.

13. The device of claim 1, wherein said sampling element is a buccal swab having an elongated shape comprising at least an elongated body to which said collecting portion is associated.

14. The device of claim 1 wherein said conserving element is a chemically-treated card suitable for conserving samples of biological material and/or is a card comprising at least a conserving substance for a sample of biological material.

* * * * *